US012697015B2

(12) United States Patent
Okada et al.

(10) Patent No.: US 12,697,015 B2
(45) Date of Patent: Aug. 4, 2026

(54) ULTRASOUND ENDOSCOPE

(71) Applicant: FUJIFILM Corporation, Tokyo (JP)

(72) Inventors: Satoru Okada, Kanagawa (JP); Yasuhiko Morimoto, Kanagawa (JP); Tsuneo Fukuzawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 232 days.

(21) Appl. No.: 18/434,712

(22) Filed: Feb. 6, 2024

(65) Prior Publication Data

US 2024/0206708 A1     Jun. 27, 2024

Related U.S. Application Data

(63) Continuation of application No. 16/831,759, filed on Mar. 26, 2020, now Pat. No. 11,925,314.

(30) Foreign Application Priority Data

Apr. 9, 2019     (JP) ................................. 2019-074385

(51) Int. Cl.
| | |
|---|---|
| *A61B 1/00* | (2006.01) |
| *A61B 1/015* | (2006.01) |
| *A61B 1/018* | (2006.01) |
| *A61B 1/05* | (2006.01) |
| *A61B 8/00* | (2006.01) |

(52) U.S. Cl.
CPC ...... *A61B 1/00119* (2013.01); *A61B 1/00011* (2013.01); *A61B 1/00082* (2013.01); *A61B 1/00091* (2013.01); *A61B 1/00094* (2013.01); *A61B 1/00098* (2013.01); *A61B 1/015* (2013.01); *A61B 1/018* (2013.01); *A61B 1/05* (2013.01); *A61B 8/4483* (2013.01); *A61B 8/5207* (2013.01)

(58) Field of Classification Search
CPC ............ A61B 1/00082; A61B 1/00091; A61B 1/00119; A61B 1/015; A61B 1/018; A61B 1/05
See application file for complete search history.

(56) References Cited

U.S. PATENT DOCUMENTS

| | | | |
|---|---|---|---|
| 2015/0011831 A1* | 1/2015 | Ouchi ...................... | A61B 1/05 |
| | | | 600/159 |
| 2017/0014099 A1* | 1/2017 | Morimoto ............ | A61B 1/0008 |

* cited by examiner

*Primary Examiner* — Aaron B Fairchild
(74) *Attorney, Agent, or Firm* — JCIPRNET

(57) ABSTRACT

There is provided an ultrasound endoscope of which a distal-end-part body of an insertion unit can be reduced in size.

In an ultrasound endoscope according to an embodiment of the invention, a straight pipe portion of a first three-way pipe and a straight pipe portion of a second three-way pipe are arranged adjacent to each other in a direction orthogonal to the direction of a longitudinal axis of an insertion unit, and a branch pipe portion and the straight pipe portion are arranged at positions overlapping with each other in a case where the first three-way pipe and the second three-way pipe are projected onto a plane perpendicular to the direction of the longitudinal axis.

13 Claims, 10 Drawing Sheets

FIG. 5

ULTRASOUND ENDOSCOPE

CROSS-REFERENCE TO RELATED APPLICATION

This application is a continuation application of and claims the priority benefit of a prior application Ser. No. 16/831,759, filed on Mar. 26, 2020, now allowed, which claims priority under 35 U.S.C. §119(a) to Japanese Patent Application No. 2019-074385 filed on Apr. 9, 2019, which is hereby expressly incorporated by reference, in its entirety, into the present application.

BACKGROUND OF THE INVENTION

1. Field of the Invention

The present invention relates to an ultrasound endoscope, and more particularly, to an ultrasound endoscope where a balloon can be mounted on a distal-end-part body of an insertion unit to be inserted into a body cavity.

2. Description of the Related Art

In the related art, an ultrasound endoscope used in a medical field includes an image pickup element and a plurality of ultrasound transducers that are integrally arranged at a distal-end-part body of an insertion unit to be inserted into a body cavity of an examinee. Each of the ultrasound transducers generates ultrasound toward a portion to be observed in the body cavity and receives ultrasound echoes (echo signals) reflected by the portion to be observed, and electrical signals (ultrasound detection signals) corresponding to the received ultrasound echoes are output to an ultrasound observation device (ultrasound processor device). Then, after the electrical signals are subjected to various kinds of signal processing in the ultrasound observation device, the electrical signals are displayed on a monitor or the like as an ultrasound tomographic image. Further, since the ultrasound and the echo signals are significantly attenuated in the air, an ultrasound transmission medium (for example, water, oil, or the like) needs to be interposed between the ultrasound transducers and the portion to be observed.

In an ultrasound endoscope disclosed in, for example, JP6170240B, a stretchable bag-shaped balloon is mounted on a distal-end-part body of the ultrasound endoscope, and an ultrasound transmission medium is injected into the balloon so that the balloon is inflated and comes into contact with the portion to be observed. Accordingly, air is excluded from a space between the ultrasound transducers and the portion to be observed, so that the attenuation of the ultrasound and the echo signals is prevented.

A supply/discharge pipe line for a balloon is inserted into an insertion unit in order to supply/suck and discharge an ultrasound transmission medium into/from the balloon. The distal end of the supply/discharge pipe line for a balloon includes a supply/discharge port opened to the distal-end-part body of the insertion unit, and an ultrasound transmission medium is supplied into and sucked and discharged from the balloon through the supply/discharge port. The proximal end of the supply/discharge pipe line for a balloon is connected to a balloon-water supply pipe line and a balloon-drain pipe line.

Further, an air/water supply pipe line is inserted into the insertion unit in order to wash an observation window provided on the distal-end-part body of the insertion unit.

The distal end of the air/water supply pipe line includes an air/water supply port opened to the distal-end-part body of the insertion unit, a nozzle is connected to the air/water supply port, and water or air is jetted toward the observation window through the nozzle. The proximal end of the air/water supply pipe line is also connected to an air supply pipe line and a water supply pipe line.

In an ultrasound endoscope disclosed in JP2000-287974A, an air supply tube, a liquid supply tube, a liquid injection tube, and a drain tube are inserted into and arranged in an insertion unit, the air supply tube and the liquid supply tube are joined and connected to one pipe line by a first bifurcated connecting pipe, and the liquid injection tube and the drain tube are joined and connected to one pipe line by a second bifurcated connecting pipe. Further, JP2000-287974A discloses that the two bifurcated connecting pipes are formed to have the same shape and the same dimensions.

SUMMARY OF THE INVENTION

In the ultrasound endoscope where the two bifurcated connecting pipes are arranged in the insertion unit as in JP2000-287974A, in terms of improving drainage performance and the durability of the ultrasound endoscope, a case where the two bifurcated connecting pipes are arranged in a hard distal-end-part body is more preferable than a case where the two bifurcated connecting pipes are arranged in a soft part of the insertion unit.

However, there is a problem that the size of the distal-end-part body is increased depending on the arrangement positions of the two bifurcated connecting pipes in a case where the two bifurcated connecting pipes are arranged in the distal-end-part body of the insertion unit.

The invention has been made in consideration of the above-mentioned circumstances, and an object of the invention is to provide an ultrasound endoscope of which a distal-end-part body of an insertion unit can be reduced in size.

In order to achieve the object of the invention, an ultrasound endoscope according to an aspect of the invention comprises a distal-end-part body that is provided on a distal end side of an insertion unit of an endoscope in a direction of a longitudinal axis, a first opening portion that is provided in the distal-end-part body, a second opening portion that is provided in the distal-end-part body, a first pipe that is connected to the first opening portion, and a second pipe that is connected to the second opening portion. The first pipe includes a first main pipe portion of which one end is connected to the first opening portion, and a first branch pipe portion that is branched from a first branch position present in a middle of the first main pipe portion. The first main pipe portion is a linear pipe line portion extending in a direction of a first pipe axis. The first branch pipe portion includes a first straight pipe portion that is offset from the first main pipe portion in a direction orthogonal to the direction of the first pipe axis by a first offset distance and extends in the direction of the first pipe axis, and a first connecting pipe portion that connects the first main pipe portion to the first straight pipe portion. The second pipe includes a second main pipe portion of which one end is connected to the second opening portion, and a second branch pipe portion that is branched from a second branch position present in a middle of the second main pipe portion. The second main pipe portion includes a second straight pipe portion of which one end is connected to the second opening portion and which extends in a direction of a second pipe axis, a third straight pipe portion that is offset from the second straight pipe portion in a direction orthogonal to the direction of the second pipe axis by a second offset distance and extends in the direction of the second pipe axis, and a second connecting pipe portion that connects the second straight pipe portion to the third straight pipe portion. The second branch pipe portion is a linear pipe line portion that is offset from the second straight pipe portion in the direction orthogonal to the direction of the second pipe axis by a third offset distance shorter than the second offset distance and extends in the direction of the second pipe axis. One end of the second branch pipe portion is connected to the second connecting pipe portion. A pipe line portion of the first main pipe portion, which is closer to the first opening portion than the first branch position, and the second straight pipe portion are arranged adjacent to each other in a direction orthogonal to the direction of the longitudinal axis. The first branch pipe portion and the second straight pipe portion are arranged at positions overlapping with each other in a case where the first pipe and the second pipe are projected onto a plane perpendicular to the direction of the longitudinal axis.

According to an aspect of the invention, it is preferable that the second straight pipe portion is disposed closer to the distal end side than the first branch position in the direction of the longitudinal axis.

According to an aspect of the invention, it is preferable that the third offset distance is longer than the first offset distance.

According to an aspect of the invention, it is preferable that the second connecting pipe portion includes a first curved pipe portion disposed at one end thereof and a second curved pipe portion disposed at the other end thereof, the other end of the second straight pipe portion is connected to the first curved pipe portion and one end of the third straight pipe portion is connected to the second curved pipe portion, and the second branch position is provided on a pipe line portion that includes the first curved pipe portion and the second curved pipe portion.

According to an aspect of the invention, it is preferable that the second connecting pipe portion includes a first curved pipe portion disposed at one end thereof, a second curved pipe portion disposed at the other end thereof, and a straight connecting pipe portion of which one end is connected to the other end of the first curved pipe portion and the other end is connected to one end of the second curved pipe portion, and the second branch position is provided on the straight connecting pipe portion.

According to an aspect of the invention, it is preferable that the first main pipe portion and the first branch pipe portion are arranged along a first imaginary plane, the second main pipe portion and the second branch pipe portion are arranged along a second imaginary plane, and the first imaginary plane and the second imaginary plane are not parallel to each other.

According to an aspect of the invention, it is preferable that the first main pipe portion, the first straight pipe portion, and the second straight pipe portion are arranged along a same straight line and the second branch pipe portion and the third straight pipe portion are arranged at positions away from the same straight line in a case where the first pipe and the second pipe are projected onto a plane perpendicular to the direction of the longitudinal axis.

According to an aspect of the invention, it is preferable that the distal-end-part body includes an ultrasound observation unit, a balloon mounting portion on which a balloon wrapping the ultrasound observation unit is attachably and detachably mounted, and an endoscopic observation unit, the ultrasound observation unit is disposed closer to the distal end side than the balloon mounting portion in the direction of the longitudinal axis, the endoscopic observation unit is disposed closer to a proximal end side than the balloon mounting portion in the direction of the longitudinal axis, the ultrasound observation unit is provided with the first opening portion, the endoscopic observation unit is provided with the second opening portion, one of the first main pipe portion and the first branch pipe portion forms a water supply passage supplying liquid to the first opening portion, and the other thereof forms a suction passage sucking the liquid from the first opening portion, and one of the third straight pipe portion and the second branch pipe portion forms an air supply passage supplying air to the second opening portion, and the other thereof forms a water supply passage supplying liquid to the second opening portion.

According to an aspect of the invention, it is preferable that the first main pipe portion forms the suction passage and the first branch pipe portion forms the water supply passage.

According to an aspect of the invention, it is preferable that the ultrasound observation unit includes an ultrasound transducer, the endoscopic observation unit includes an observation window and an illumination window, and a nozzle of which a jet port faces the observation window is mounted on the second opening portion.

According to the invention, the size of the distal-end-part body of the insertion unit can be reduced.

BRIEF DESCRIPTION OF THE DRAWINGS

FIG. 5 is a perspective view of a plurality of contents arranged in the distal-end-part body.

DESCRIPTION OF THE PREFERRED EMBODIMENTS

An ultrasound endoscope according to an embodiment of the invention will be described below with reference to the accompanying drawings.

Figure 1:
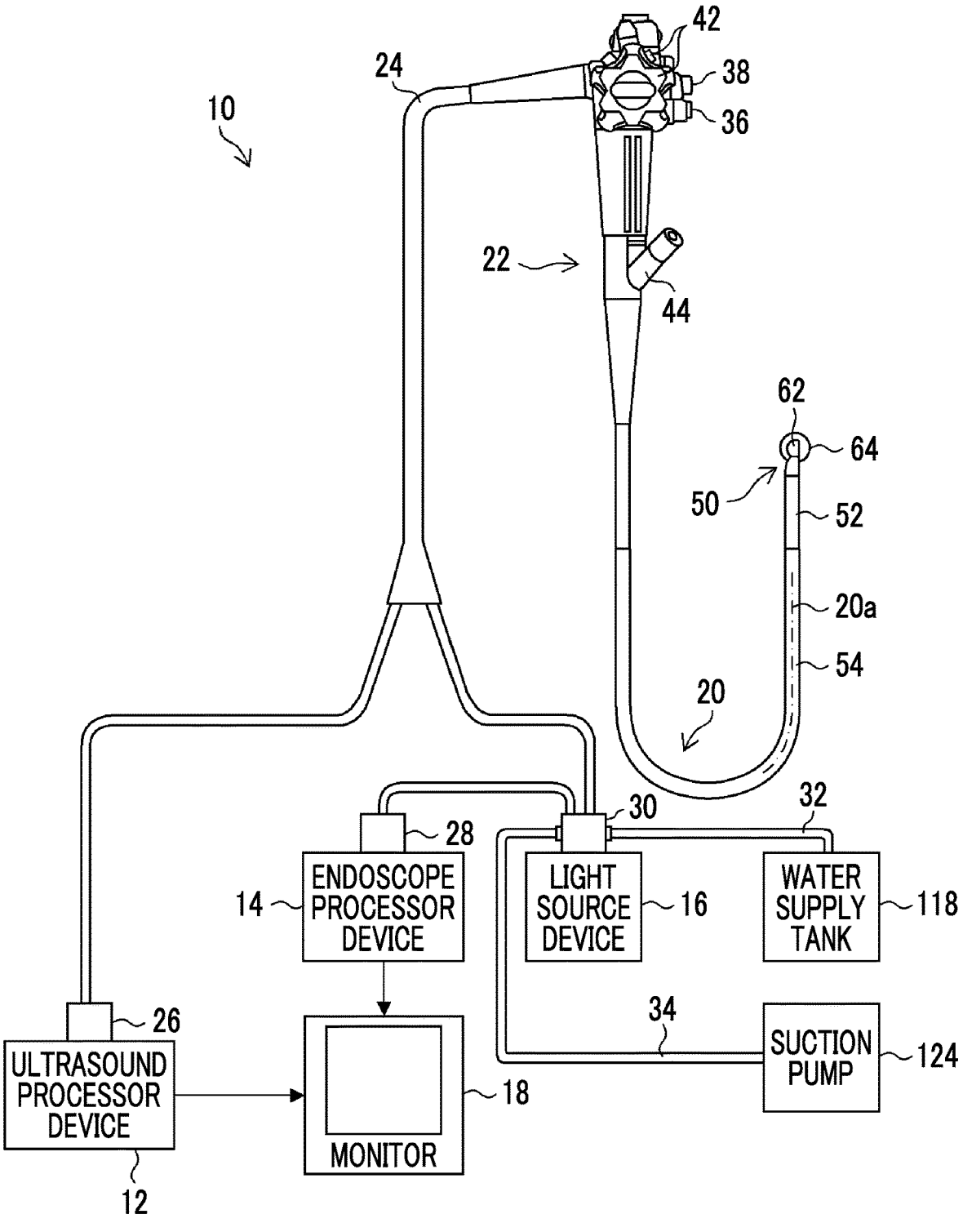
FIG. 1 is a diagram showing the configuration of an ultrasonography system to which an ultrasound endoscope according to an embodiment is applied.

FIG. 1 is a diagram showing the configuration of an ultrasonography system 2 to which an ultrasound endoscope 10 according to an embodiment is applied.

As shown in FIG. 1, the ultrasonography system 2 comprises an ultrasound endoscope 10, an ultrasound processor device 12 that generates an ultrasound image, an endoscope processor device 14 that generates an endoscopic image, a light source device 16 that supplies illumination light for illuminating the inside of a body cavity to the ultrasound endoscope 10, and a monitor 18 that displays the ultrasound image and the endoscopic image.

The ultrasound endoscope 10 includes an insertion unit 20 that is to be inserted into the body cavity of an examinee, an operation unit 22 that is connected to a proximal end portion of the insertion unit 20 and is operated by an operator, and a universal cord 24 of which one end is connected to the operation unit 22. The other end of the universal cord 24 is provided with an ultrasound connector 26 that is connected to the ultrasound processor device 12, an endoscope connector 28 that is connected to the endoscope processor device 14, and a light source connector 30 that is connected to the light source device 16. The ultrasound endoscope 10 is attachably and detachably connected to the ultrasound processor device 12, the endoscope processor device 14, and the light source device 16 through the respective connectors 26, 28, and 30. Further, a tube 32 for supplying air and water and a tube 34 for suction are connected to the light source connector 30.

The monitor 18 receives video signals that are generated by the ultrasound processor device 12 and the endoscope processor device 14 and displays the ultrasound image and the endoscopic image. In regard to the display of the ultrasound image and the endoscopic image, only one of the ultrasound image and the endoscopic image can be appropriately switched and displayed on the monitor 18 or both of the images can be simultaneously displayed.

The operation unit 22 is provided with an air/water supply button 36 and a suction button 38 that are arranged in parallel, a pair of angle knobs 42 and 42, and a treatment tool insertion opening 44.

The insertion unit 20 has a distal end, a proximal end, and a longitudinal axis 20a, and includes a distal-end-part body 50, a bendable part 52, and a soft part 54 that are arranged in this order from the distal end side. The distal-end-part body 50 is formed of a hard member. The bendable part 52 is connected to the proximal end side of the distal-end-part body 50. The soft part 54 connects the proximal end side of the bendable part 52 to the distal end side of the operation unit 22, is thin and long, and has flexibility. That is, the distal-end-part body 50 is provided on the distal end side of the insertion unit 20 in the direction of the longitudinal axis 20a. Further, the bendable part 52 is remotely operated to be bent by the rotation of the pair of angle knobs 42 and 42 of the operation unit 22. Accordingly, the distal-end-part body 50 can be directed in a desired direction. Furthermore, a balloon 64 to be described later is attachably and detachably mounted on the distal-end-part body 50.

Figure 2:
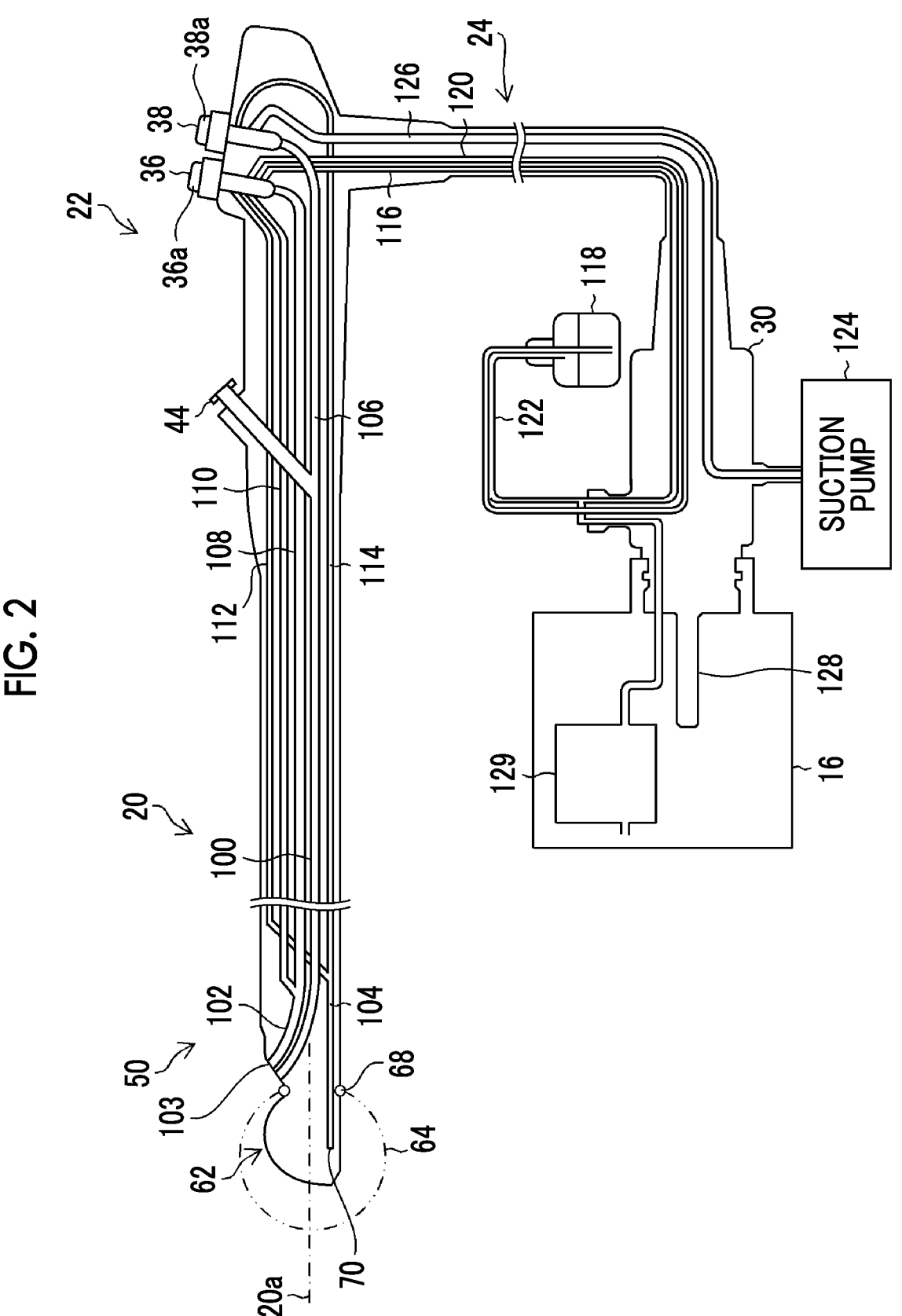
FIG. 2 is a diagram showing the configuration of pipe lines of the ultrasound endoscope.

Here, the configuration of pipe lines of the ultrasound endoscope 10 will be described. FIG. 2 is a diagram showing the configuration of pipe lines of the ultrasound endoscope 10.

As shown in FIG. 2, a treatment tool channel 100, an air/water supply pipe line 102, and a balloon pipe line 104 of which one end communicates with the internal space of the balloon 64 are provided in the insertion unit 20 and the operation unit 22.

One end of the treatment tool channel 100 is connected to a treatment tool outlet 94 (see FIG. 3) to be described later, and the other end thereof is connected to the treatment tool insertion opening 44 of the operation unit 22. Further, a suction pipe line 106 is branched from the treatment tool channel 100, and is connected to the suction button 38 of the operation unit 22.

One end of the air/water supply pipe line 102 is connected to an air/water supply port 103 provided in the distal-end-part body 50, and a nozzle 92 (see FIG. 3) to be described later is connected to the air/water supply port 103. The other end of the air/water supply pipe line 102 is connected to an air supply pipe line 108 and a water supply pipe line 110. The air supply pipe line 108 and the water supply pipe line 110 are connected to the air/water supply button 36 of the operation unit 22. Here, the air/water supply port 103 is an example of a second opening portion of the invention. Further, the air supply pipe line 108 forms an air supply passage that supplies air to the air/water supply port 103, and the water supply pipe line 110 forms a water supply passage that supplies liquid to the air/water supply port 103.

One end of the balloon pipe line 104 is connected to a supply/discharge port 70 provided in the distal-end-part body 50, and the other end thereof is connected to a balloon-water supply pipe line 112 and a balloon-drain pipe line 114. The balloon-water supply pipe line 112 is connected to the air/water supply button 36, and the balloon-drain pipe line 114 is connected to the suction button 38. Here, the supply/discharge port 70 is an example of a first opening portion of the invention. Further, the balloon-water supply pipe line 112 forms a water supply passage that supplies liquid to the supply/discharge port 70, and the balloon-drain pipe line 114 forms a suction passage that sucks liquid from the supply/discharge port 70.

One end of an air supply source-pipe line 116 communicating with an air supply pump 129 and one end of a water supply source-pipe line 120 communicating with a water supply tank 118 are connected to the air/water supply button 36 in addition to the air supply pipe line 108, the water supply pipe line 110, and the balloon-water supply pipe line 112. The air supply pump 129 is always operated during ultrasound observation.

A branch pipe line 122 is branched from the air supply source-pipe line 116, and is connected to the inlet of the water supply tank 118 (above the liquid level). Further, the other end of the water supply source-pipe line 120 is inserted into the water supply tank 118 (below the liquid level). Then, in a case where the internal pressure of the water supply tank 118 is increased by the supply of air from the air supply pump 129 through the branch pipe line 122, water present in the water supply tank 118 is supplied to the water supply source-pipe line 120.

The air/water supply button 36 is a so-called two-stage switching button. Although not shown, an air outlet communicating with the atmosphere is formed at an operation cap 36a of the air/water supply button 36. In a case where the operation cap 36a is not operated, the air/water supply button 36 allows the water supply source-pipe line 120 to be closed and allows the air supply source-pipe line 116 to communicate with the air outlet of the operation cap 36a. Accordingly, air supplied from the air supply source-pipe line 116 leaks from the air outlet of the air/water supply button 36. Then, in a case where the air outlet is closed in this state, the air supply source-pipe line 116 and the air supply pipe line 108 communicate with each other in a state in which the water supply source-pipe line 120 continues to be closed. Accordingly, air is supplied to the air/water supply pipe line 102 from the air supply pipe line 108 and is jetted from the air/water supply port 103.

Further, in a case where the operation cap 36a is half pressed, the air/water supply button 36 allows the air supply source-pipe line 116 to be closed and allows the water supply source-pipe line 120 to communicate with only the water supply pipe line 110. Accordingly, water supplied from the water supply source-pipe line 120 is supplied to the air/water supply pipe line 102 from the water supply pipe line 110, and is jetted from the air/water supply port 103. Then, in a case where the operation cap 36a is fully pressed, the air/water supply button 36 allows the water supply source-pipe line 120 to communicate with only the balloon-water supply pipe line 112 in a state in which the air supply source-pipe line 116 continues to be closed. Accordingly, water supplied from the water supply source-pipe line 120 is supplied to the balloon pipe line 104 from the balloon-water supply pipe line 112, and is supplied into the balloon 64 from the supply/discharge port 70.

One end of a suction source-pipe line 126 of which the other end communicates with a suction pump 124 is connected to the suction button 38 in addition to the suction pipe line 106 and the balloon-drain pipe line 114. The suction pump 124 is also always operated during ultrasound observation. The suction button 38 is a two-stage switching button like the air/water supply button 36.

In a case where an operation cap 38a of the suction button 38 is not operated, the suction button 38 allows the suction source-pipe line 126 to communicate with the outside (the atmosphere). Further, in a case where the operation cap 38a is half pressed, the suction button 38 allows the suction source-pipe line 126 to communicate with only the suction pipe line 106. Accordingly, the negative pressure-suction forces of the suction pipe line 106 and the treatment tool channel 100 are increased, so that various materials to be sucked are sucked from the treatment tool outlet 94 (see FIG. 3). Then, in a case where the operation cap 38a is fully pressed, the suction button 38 allows the suction source-pipe line 126 to communicate with only the balloon-drain pipe line 114. Accordingly, the negative pressure-suction forces of the balloon-drain pipe line 114 and the balloon pipe line 104 are increased, so that water present in the balloon 64 is sucked and drained from the supply/discharge port 70.

Figure 3:
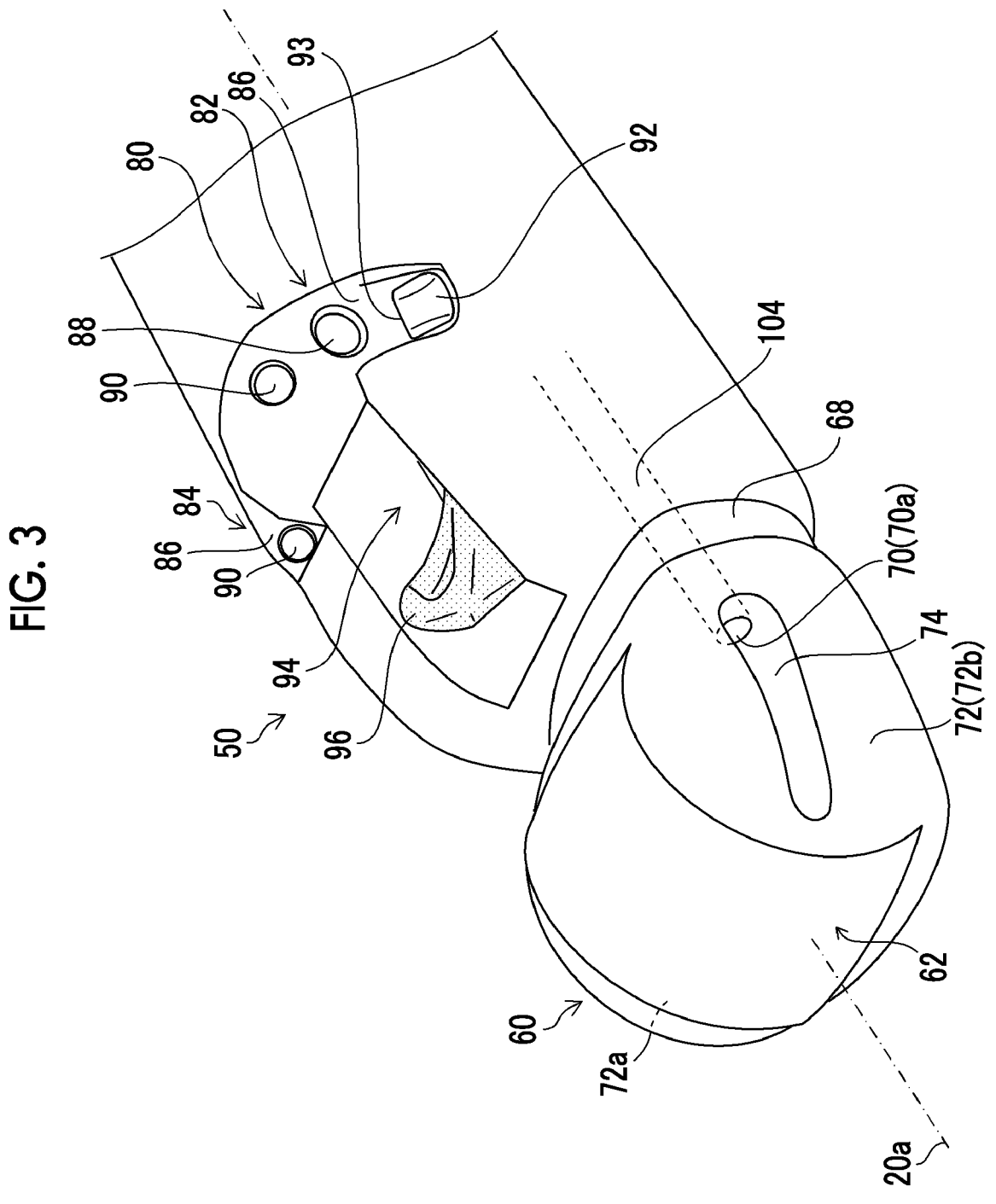
FIG. 3 is a perspective view of a distal-end-part body of an insertion unit of the ultrasound endoscope.

Next, the configuration of the distal-end-part body 50 of the ultrasound endoscope 10 will be described in detail. FIG. 3 is a perspective view of the distal-end-part body 50 and FIG. 4 is a side view of the distal-end-part body 50.

Figure 4:
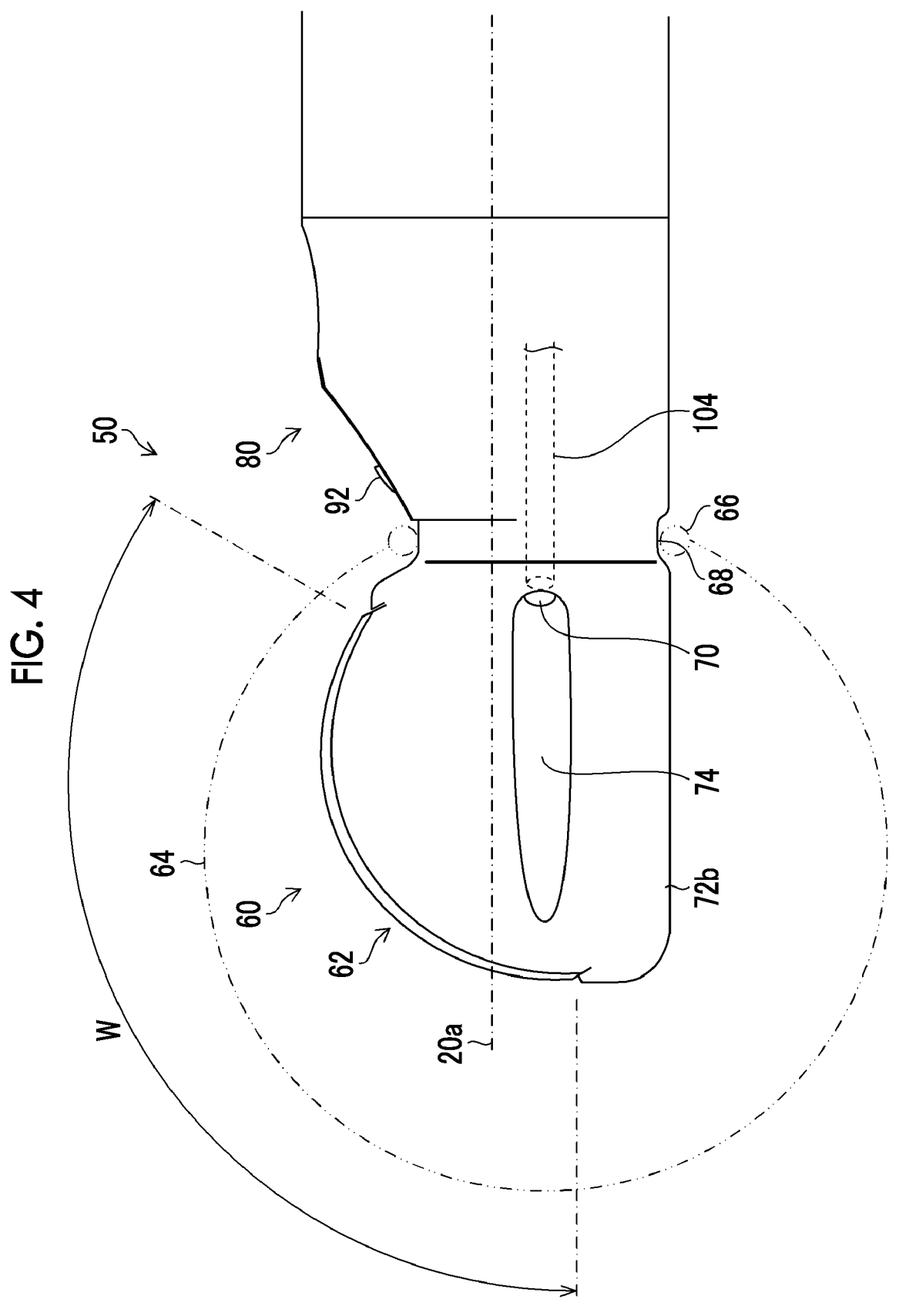
FIG. 4 is a side view of the distal-end-part body of the insertion unit of the ultrasound endoscope.

As shown in FIGS. 3 and 4, the distal-end-part body 50 of the ultrasound endoscope 10 is provided with an ultrasound observation unit 60 that acquires an ultrasound image, a locking groove 68 to which the balloon 64 wrapping the ultrasound observation unit 60 is attachably and detachably connected, and an endoscopic observation unit 80 that acquires an endoscopic image. Further, the ultrasound observation unit 60 is disposed closer to the distal end side than the locking groove 68, which forms a balloon mounting portion, in the direction of the longitudinal axis 20a, and the endoscopic observation unit 80 is disposed closer to the proximal end side than the locking groove 68 in the direction of the longitudinal axis 20a. Furthermore, the ultrasound observation unit 60 is provided with the supply/discharge port 70, and the endoscopic observation unit 80 is provided with the air/water supply port 103 (see FIG. 1).

The ultrasound observation unit 60 comprises an ultrasound transducer 62 that includes a plurality of ultrasound vibrators. The respective ultrasound vibrators of the ultrasound transducer 62 are arranged at regular intervals in the shape of a convex curve along the longitudinal axis 20a, and are sequentially driven on the basis of drive signals that are input from the ultrasound processor device 12 (see FIG. 1). Accordingly, convex electronic scanning is performed over a scanning range shown in FIG. 4 by W. In a case where the respective ultrasound vibrators are driven, the ultrasound vibrators sequentially generate ultrasound toward a portion to be observed, receive ultrasound echoes (echo signals) reflected by the portion to be observed, and output electrical signals (ultrasound detection signals), which correspond to the received ultrasound echoes, to the ultrasound processor device 12 (see FIG. 1) through an ultrasound cable 130 (see FIGS. 5 and 6). Then, after various kinds of signal processing are performed in the ultrasound processor device 12, the electrical signals are displayed on the monitor 18 as the ultrasound image.

A bag-shaped balloon 64, which covers and wraps the ultrasound transducer 62, is mounted on the distal-end-part body 50 to prevent the attenuation of the ultrasound and the ultrasound echoes (echo signals) (see FIG. 4). The balloon 64 is made of a stretchable elastic material, and a stretchable locking ring 66 is formed at an open end of the balloon 64. Meanwhile, the distal-end-part body 50 is provided with the above-mentioned locking groove 68, and the locking groove 68 is formed of an annular groove portion that is formed over the entire circumference (outer periphery) of the distal-end-part body 50 in a circumferential direction having a center on the longitudinal axis 20a. The locking ring 66 is fitted to the locking groove 68, so that the balloon 64 is attachably and detachably mounted on the distal-end-part body 50.

The balloon 64 is inserted into the body cavity in a state in which the balloon 64 contracts so as to be in close contact with the outer wall surface of the distal-end-part body 50. Then, in a case where an operator is to generate ultrasound toward the portion to be observed from the respective ultrasound vibrators of the ultrasound transducer 62, the operator supplies water, which is present in the water supply tank 118, into the balloon 64 from the balloon-water supply pipe line 112 (see FIG. 5) through the balloon pipe line 104 by fully pressing the operation cap 36a of the air/water supply button 36 to inflate the balloon 64 until the balloon 64 comes into contact with the inner wall of the body cavity. Accordingly, since a space between the portion to be observed and the ultrasound transducer 62 is filled with water that is an ultrasound transmission medium, the balloon 64 improves the adhesiveness of the distal-end-part body 50 to the inner wall of the body cavity and prevents the ultrasound, which is generated from the respective ultrasound vibrators of the ultrasound transducer 62, and the ultrasound echoes from being attenuated by air. Further, in a case where an operator is to draw the insertion unit 20 to the outside from the body cavity, the operator sucks and discharges water, which is present in the balloon 64, through the balloon pipe line 104, the balloon-drain pipe line 114, and the like by fully pressing the operation cap 38a of the suction button 38 to allow the balloon 64 to contract so that the balloon 64 is in close contact with the outer wall surface of the distal-end-part body 50 as in a case where the operator is to insert the insertion unit 20 into the body cavity.

For example, latex rubber is used for the balloon 64. Further, it is preferable that water as the ultrasound transmission medium supplied into the balloon 64 is deaerated water from which dissolved gas has been removed. Furthermore, an ultrasound transmission medium, such as oil, other than water may be supplied into the balloon 64.

The balloon pipe line 104 is disposed in the distal-end-part body 50, and the supply/discharge port 70 is provided on the distal end side of the balloon pipe line 104. The supply/discharge port 70 is formed in a housing member 72 holding the ultrasound transducer 62. Specifically, the housing member 72 includes a pair of side wall portions 72a and 72b facing each other with the ultrasound transducer 62 interposed between, and a groove portion 74 is formed on the side wall portion 72*b*, which is positioned on the right side in a case where the distal-end-part body 50 is viewed from the distal end side, of the pair of side wall portions 72*a* and 72*b*. Further, the supply/discharge port 70 is provided on the proximal end face of the groove portion 74 in the direction of the longitudinal axis 20*a*. This proximal end face is formed to face the distal end side in the direction of the longitudinal axis 20*a*.

The groove portion 74 is provided on the side wall portion 72*b* in the example shown in FIGS. 3 and 4, but the groove portion 74 may be provided on the side wall portion 72*a* that is positioned on the left side in a case where the distal-end-part body 50 is viewed from the distal end side. Furthermore, the groove portion 74 may be formed toward the distal end side in the direction of the longitudinal axis 20*a* from the locking groove 68 as a starting point.

Meanwhile, the endoscopic observation unit 80 includes an observation portion 82 and an illumination portion 84, and the observation portion 82 and the illumination portion 84 are arranged on an inclined surface portion 86 that is formed on the distal-end-part body 50 so as to be inclined with respect to the direction of the longitudinal axis 20*a* toward the proximal end side from the locking groove 68.

The observation portion 82 includes an observation window 88; and an objective lens of an observation optical system and an image pickup element, such as a charge coupled device (CCD) or a complementary metal oxide semiconductor (CMOS), disposed at the image formation position of the objective lens are arranged in the rear of the observation window 88. A signal cable 132 (see FIGS. 5 and 6) is connected to a substrate that supports the image pickup element. As shown in FIG. 1, the signal cable 132 is inserted into the insertion unit 20 and the universal cord 24, extends up to the endoscope connector 28, and is connected to the endoscope processor device 14. An observation image, which is taken in from the observation window 88, is formed on the light-receiving surface of the image pickup element and is converted to electrical signals (image pickup signals), and the electrical signals are output to the endoscope processor device 14 through the signal cable 132 and are converted to video signals. Then, the video signals are output to the monitor 18 connected to the endoscope processor device 14, so that an endoscopic image is displayed on the screen of the monitor 18.

As shown in FIG. 3, the illumination portion 84 includes a pair of illumination windows 90 and 90, and the light-emitting ends of light guides 128 and 128 (see FIGS. 5 and 6) are arranged in the rear of the pair of illumination windows 90 and 90, respectively. The light guides 128 are inserted into the insertion unit 20 and the universal cord 24 and the incident ends of the light guides 128 are arranged in the light source connector 30 (see FIG. 2). Accordingly, in a case where the light source connector 30 is connected to the light source device 16, illumination light emitted from the light source device 16 is transmitted to the pair of illumination windows 90 and 90 through the light guides 128 and 128 and is emitted forward from the pair of illumination windows 90 and 90.

A nozzle 92 including a jet port 93 is provided near the observation window 88 on the inclined surface portion 86 of the distal-end-part body 50 in addition to the observation window 88 and the illumination windows 90 and 90. The nozzle 92 is connected to the air/water supply port 103 (see FIG. 5) so that the jet port 93 faces the surface of the observation window 88, and water and air are selectively switched and separately jetted to remove foreign materials and the like adhering to the surface of the observation window 88.

Further, the distal-end-part body 50 is provided with the treatment tool outlet 94. One end of the treatment tool channel 100 (see FIG. 2) inserted into the insertion unit 20 is connected to the treatment tool outlet 94, and a treatment tool inserted into the treatment tool insertion opening 44 is introduced into the body cavity from the treatment tool outlet 94 through the treatment tool channel 100*a*.

A standing base 96 for changing the lead-out direction of the treatment tool, which is introduced into the body cavity from the treatment tool outlet 94, is provided in the treatment tool outlet 94. One end of a wire 134 (see FIG. 6) is connected to the standing base 96, and the other end of the wire 134 is connected to a standing lever (not shown) of the operation unit 22. The standing angle of the standing base 96 is changed by an operation for pushing/pulling the wire 134 by the operation of the standing lever. Accordingly, the treatment tool is led out in a desired direction.

Figure 5:
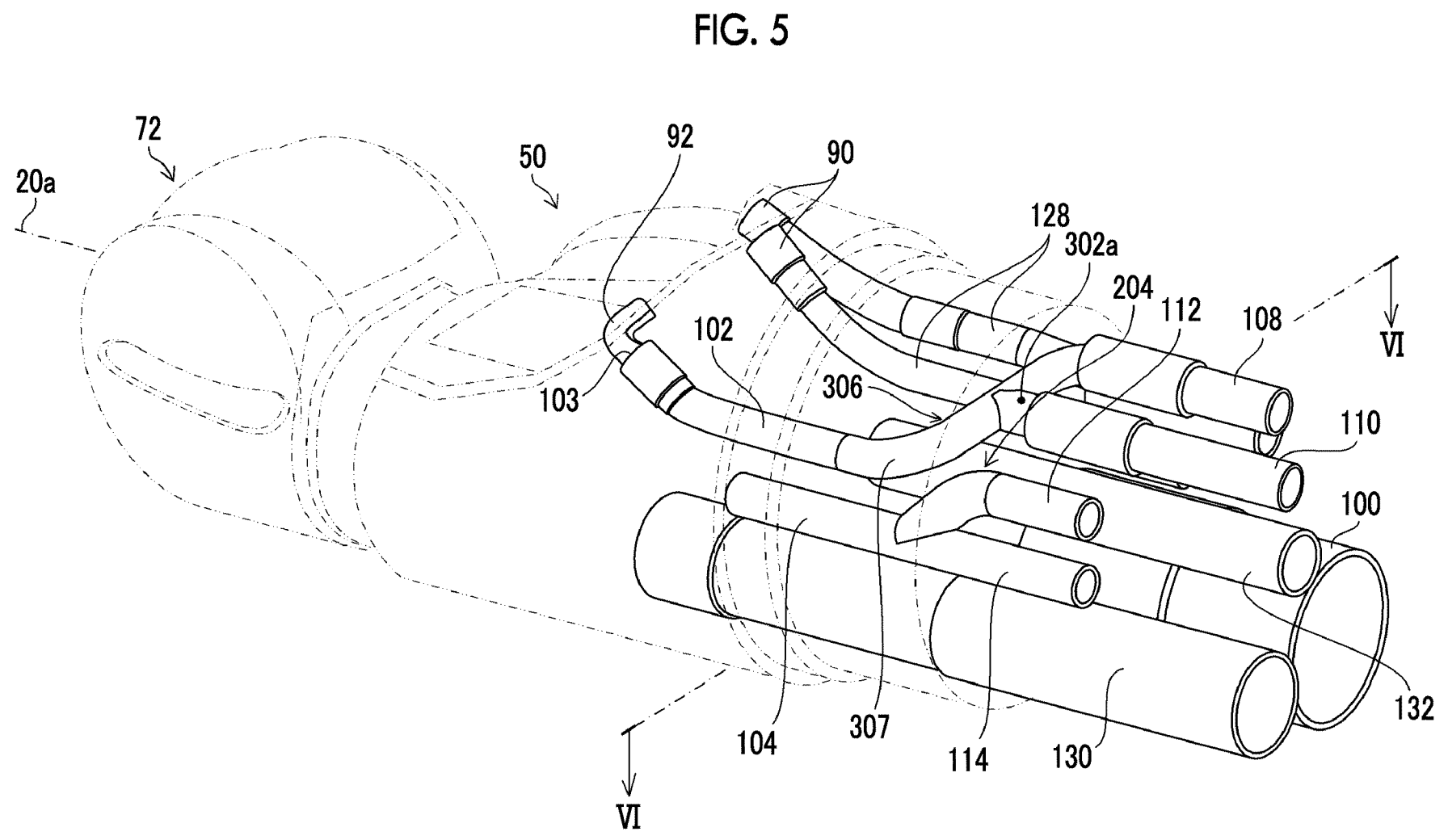

FIG. 5 is a perspective view of a plurality of contents arranged in the distal-end-part body 50. Further, FIG. 6 is a cross-sectional view taken along line VI-VI of FIG. 5, and is a cross-sectional view in a case where the arrangement positions of the contents are viewed from the proximal end side of the distal-end-part body 50.

Figure 6:
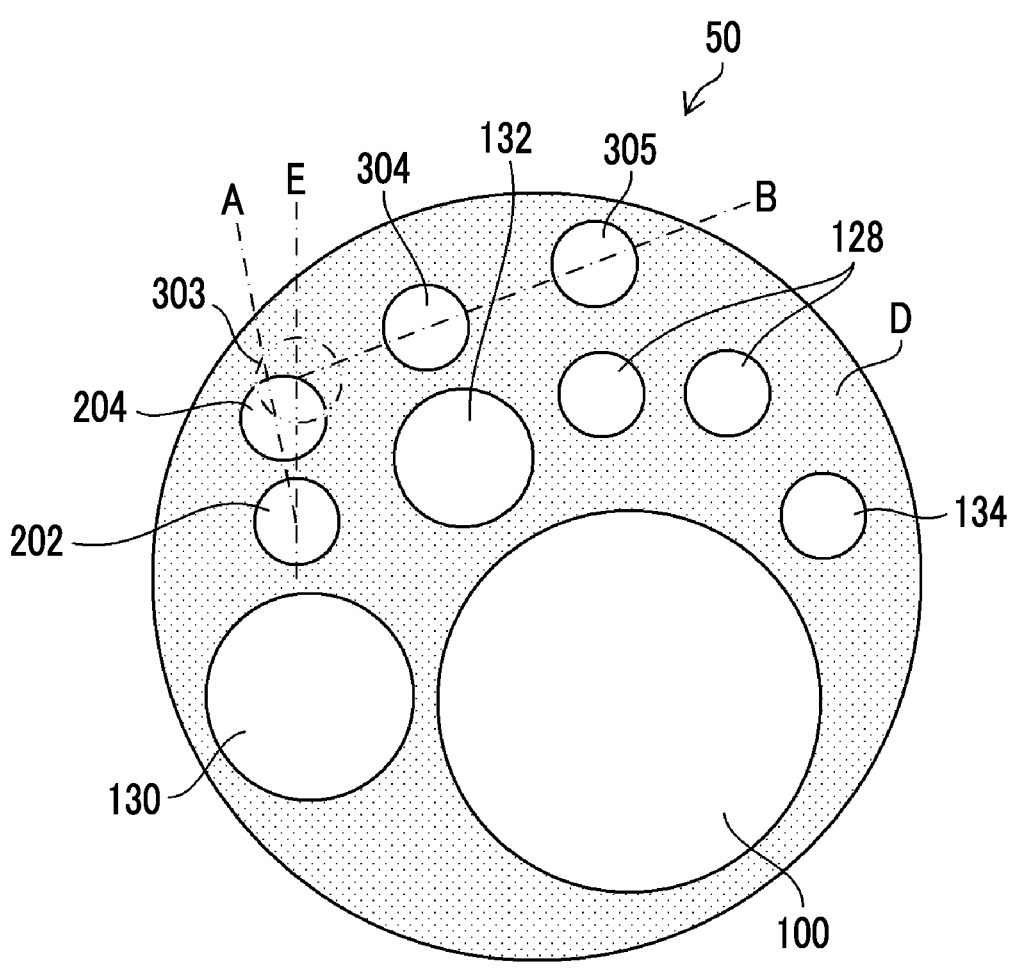
FIG. 6 is a cross-sectional view taken along line VI-VI of FIG. 5.

As shown in FIGS. 5 and 6, the contents, such as the treatment tool channel 100, the air/water supply pipe line 102, the balloon pipe line 104, the air supply pipe line 108, the water supply pipe line 110, the balloon-water supply pipe line 112, the balloon-drain pipe line 114, the light guides 128 and 128, the ultrasound cable 130, the signal cable 132, and the wire 134, are arranged at predetermined positions in the distal-end-part body 50.

Next, the arrangement configuration of the air/water supply pipe line 102, the balloon pipe line 104, the air supply pipe line 108, the water supply pipe line 110, the balloon-water supply pipe line 112, and the balloon-drain pipe line 114 arranged in the distal-end-part body 50 will be described with reference to FIGS. 7 and 8.

Figure 7:
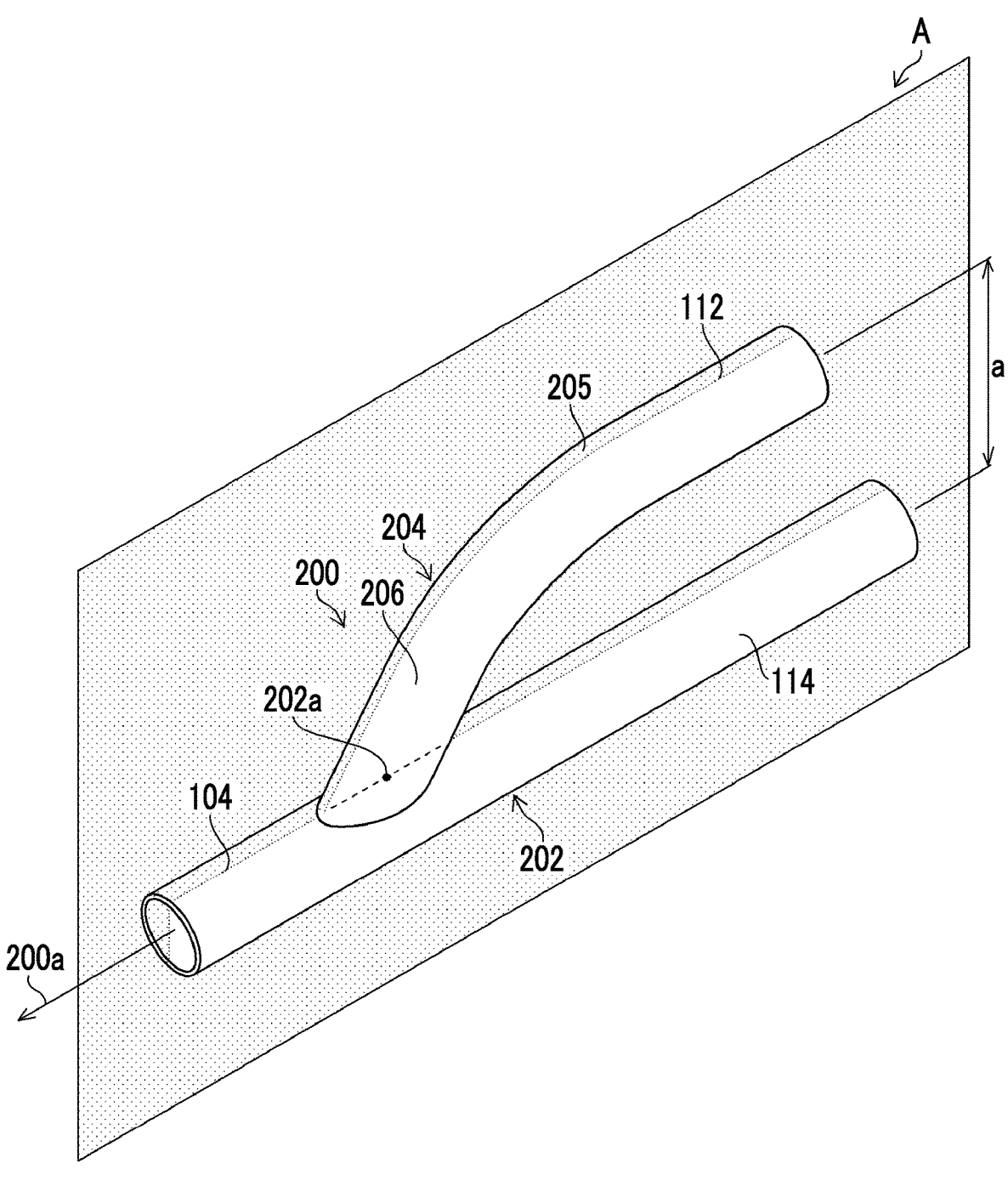
FIG. 7 is a diagram showing main portions of a first three-way pipe.

FIG. 7 is a diagram showing of a first three-way pipe 200. The first three-way pipe 200 forms a portion where the balloon pipe line 104, the balloon-water supply pipe line 112, and the balloon-drain pipe line 114 are connected. An example where a part of the balloon pipe line 104, a part of the balloon-water supply pipe line 112, and a part of the balloon-drain pipe line 114 form the first three-way pipe 200 is shown in FIG. 7, but the first three-way pipe 200 is not limited thereto. The entire balloon pipe line 104, the entire balloon-water supply pipe line 112, and the entire balloon-drain pipe line 114 may form the first three-way pipe 200. Here, the first three-way pipe 200 is an example of a first pipe of the invention. A first imaginary plane A denoted by reference character A is shown in FIG. 7, and a main pipe portion 202 and a branch pipe portion 204 are arranged along the first imaginary plane A as described later.

Figure 8:
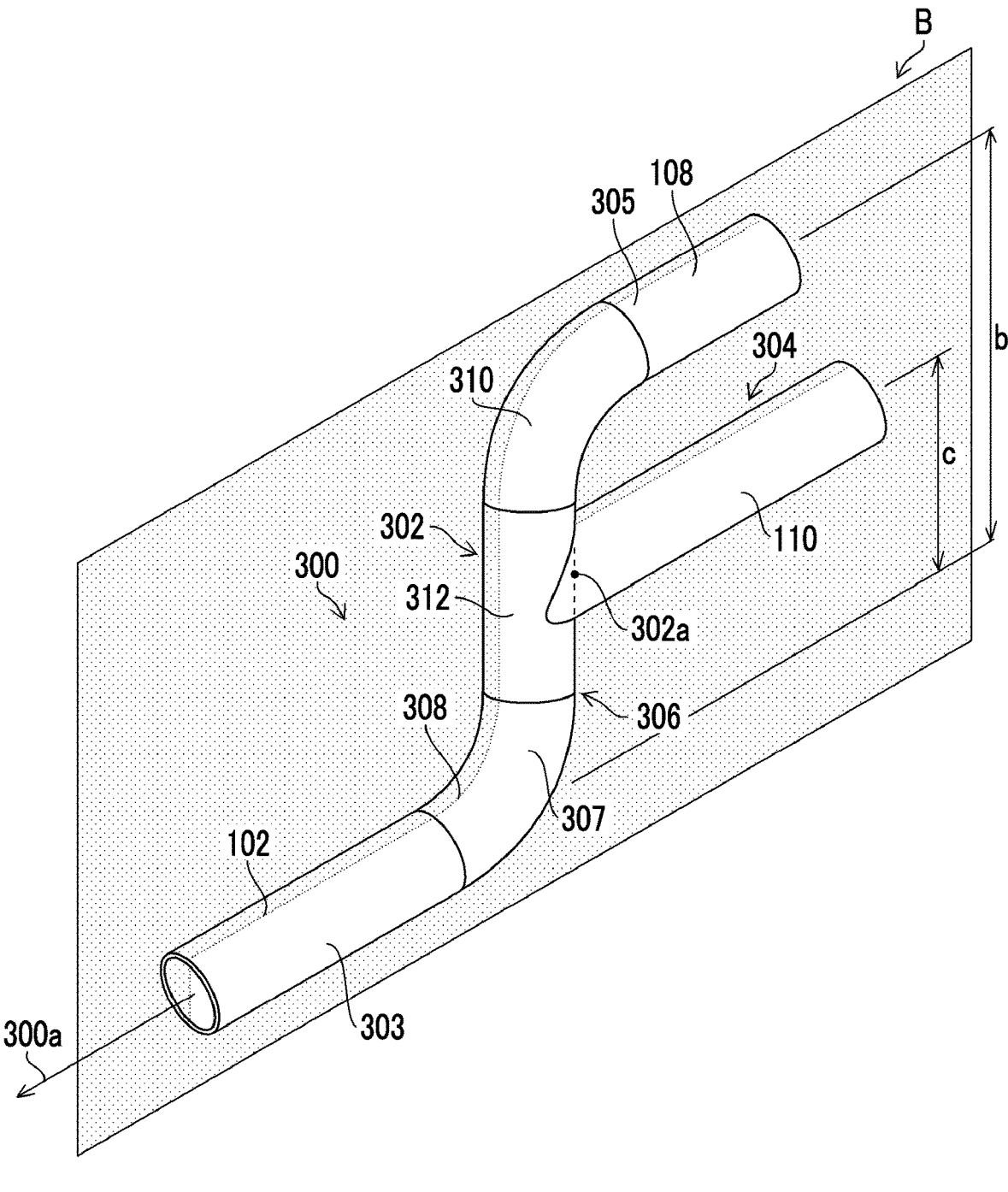
FIG. 8 is a diagram showing main portions of a second three-way pipe.

FIG. 8 is a diagram showing of a second three-way pipe 300. The second three-way pipe 300 forms a portion where the air/water supply pipe line 102, the air supply pipe line 108, and the water supply pipe line 110 are connected. An example where a part of the air/water supply pipe line 102, a part of the air supply pipe line 108, and a part of the water supply pipe line 110 form the second three-way pipe 300 is shown in FIG. 8, but the second three-way pipe 300 is not limited thereto. The entire air/water supply pipe line 102, the entire air supply pipe line 108, and the entire water supply pipe line 110 may form the second three-way pipe 300. Here, the second three-way pipe 300 is an example of a second pipe of the invention. A second imaginary plane B denoted by reference character B is shown in FIG. 8, and a main pipe portion 302 and a branch pipe portion 304 are arranged along the second imaginary plane B as described later.

First, the first three-way pipe 200 shown in FIG. 7 will be described. The first three-way pipe 200 includes the main pipe portion 202 and the branch pipe portion 204. The main pipe portion 202 is formed as a first main pipe portion of which one end is connected to the supply/discharge port 70 (see FIG. 3), and the branch pipe portion 204 is formed as a first branch pipe portion that is branched from a branch position 202a present in the middle of the main pipe portion 202. Here, the branch position 202a corresponds to a first branch position of the invention. The main pipe portion 202 may be directly connected to the supply/discharge port 70 and may be indirectly connected to the supply/discharge port 70 through other pipes.

The main pipe portion 202 forms a part of the balloon-drain pipe line 114 and the balloon pipe line 104, and is formed as a linear pipe line portion extending in the direction of a first pipe axis 200a.

The branch pipe portion 204 includes a straight pipe portion 205 and a connecting pipe portion 206. The straight pipe portion 205 is formed as a straight pipe portion that is offset from the main pipe portion 202 in a direction orthogonal to the direction of the first pipe axis 200a by a first offset distance a and extends in the direction of the first pipe axis 200a. The straight pipe portion 205 forms a part of the balloon-water supply pipe line 112, and is an example of a first straight pipe portion of the invention. Further, the connecting pipe portion 206 is formed in the shape of a curved pipe, and one end of the connecting pipe portion 206 is connected to the branch position 202a of the main pipe portion 202 and the other end thereof is connected to one end of the straight pipe portion 205. The connecting pipe portion 206 is an example of a first connecting pipe portion of the invention.

Next, the second three-way pipe 300 shown in FIG. 8 will be described. The second three-way pipe 300 includes a main pipe portion 302 of which one end is connected to the air/water supply port 103 (see FIG. 1), and a branch pipe portion 304 that is branched from a branch position 302a present in the middle of the main pipe portion 302. The main pipe portion 302 is an example of a second main pipe portion of the invention. The branch pipe portion 304 is an example of a second branch pipe portion of the invention. Further, the branch position 302a corresponds to a second branch position of the invention. The main pipe portion 302 may be directly connected to the air/water supply port 103 (see FIG. 1) and may be indirectly connected to the air/water supply port 103 through other pipes.

The main pipe portion 302 includes a straight pipe portion 303 of which one end is connected to the air/water supply port 103 and which extends in the direction of a second pipe axis 300a, a straight pipe portion 305 that is offset from the straight pipe portion 303 in a direction orthogonal to the direction of the second pipe axis 300a by a second offset distance b and extends in the direction of the second pipe axis 300a, and a connecting pipe portion 306 that connects the other end of the straight pipe portion 303 to one end of the straight pipe portion 305. The straight pipe portion 303 forms a part of the air/water supply pipe line 102, and is an example of a second straight pipe portion of the invention. Further, the straight pipe portion 305 forms a part of the air supply pipe line 108 and is an example of a third straight pipe portion of the invention. Furthermore, the branch pipe portion 304 forms a part of the water supply pipe line 110 and is an example of a second branch pipe portion of the invention.

The branch pipe portion 304 is formed as a linear pipe line portion that is offset from the straight pipe portion 303 in a direction orthogonal to the direction of the second pipe axis 300a by a third offset distance c shorter than the second offset distance b and extends in the direction of the second pipe axis 300a. One end of the branch pipe portion 304 is connected to the branch position 302a of the connecting pipe portion 306. For example, the third offset distance c shown in FIG. 8 is set to be longer than the first offset distance a shown in FIG. 7, but is not limited thereto. The third offset distance c may be set to be shorter than the first offset distance a.

Further, as shown in FIG. 8, the connecting pipe portion 306 includes a first curved pipe portion 308 disposed at one end thereof and a second curved pipe portion 310 disposed at the other end thereof and is formed in an S shape. Furthermore, the other end of the straight pipe portion 303 is connected to one end of the first curved pipe portion 308 and one end of the straight pipe portion 305 is connected to the other end of the second curved pipe portion 310.

Further, the connecting pipe portion 306 includes a straight connecting pipe portion 312 that connects the other end of the first curved pipe portion 308 to one end of the second curved pipe portion 310. One end of the straight connecting pipe portion 312 is connected to the other end of the first curved pipe portion 308, and the other end of the straight connecting pipe portion 312 is connected to one end of the second curved pipe portion 310.

Figure 9:
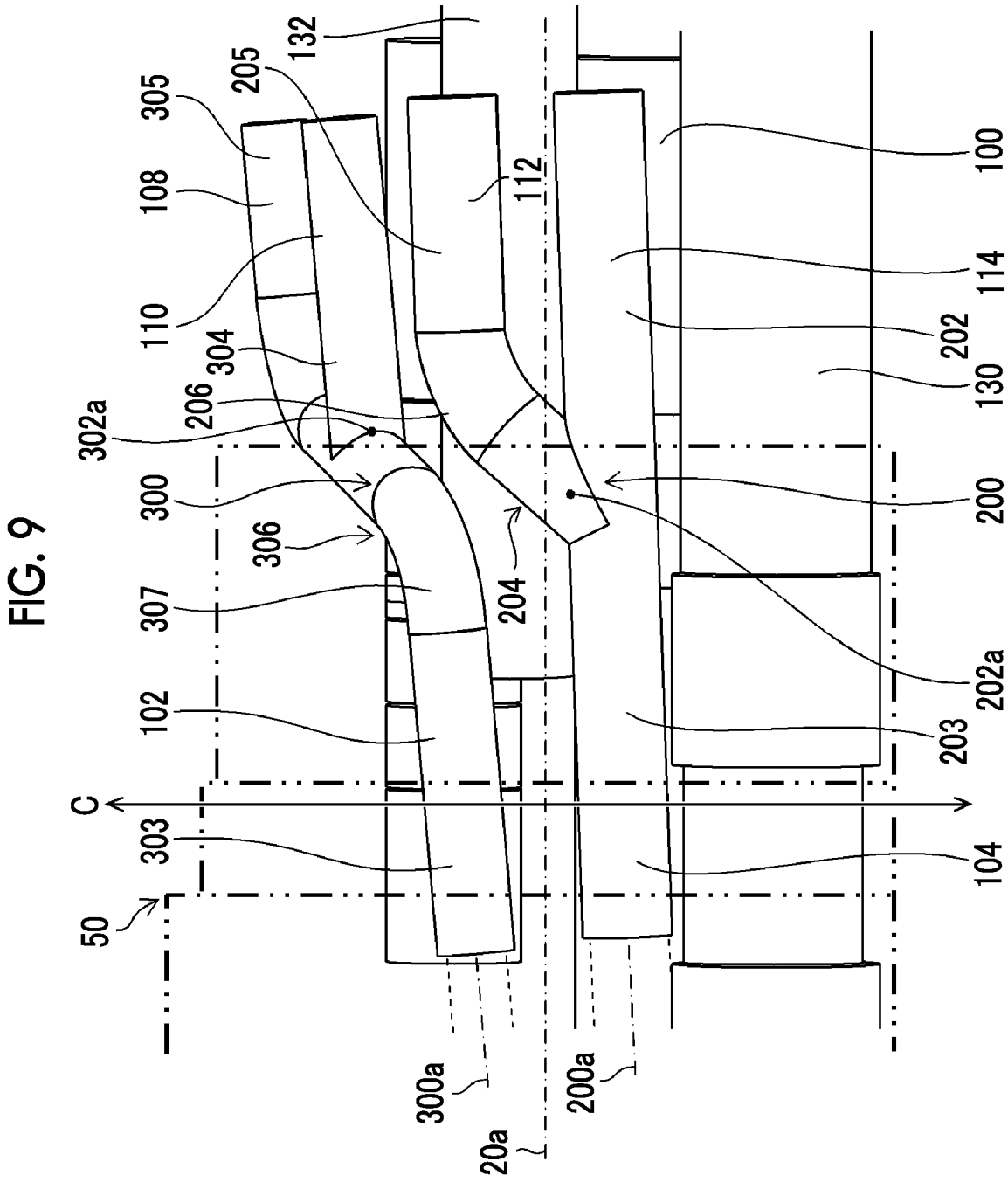
FIG. 9 is an enlarged side view of main portions of the distal-end-part body that shows the arrangement positions of the first three-way pipe and the second three-way pipe.

FIG. 9 is an enlarged side view of main portions of the distal-end-part body 50 that shows the arrangement positions of the first three-way pipe 200 and the second three-way pipe 300 of the distal-end-part body 50.

In the ultrasound endoscope 10 according to the embodiment, the first three-way pipe 200 and the second three-way pipe 300 are arranged at the following positions to reduce the size of the distal-end-part body 50 in a case where the first three-way pipe 200 and the second three-way pipe 300 having the above-mentioned configuration are arranged in the distal-end-part body 50.

As shown in FIG. 9, the pipe line portion 203 closer to the supply/discharge port 70 (see FIG. 4) than the branch position 202a of the main pipe portion 202 and the straight pipe portion 303 are arranged adjacent to each other in the direction of an arrow C (hereinafter, referred to as "the height direction of the distal-end-part body 50") orthogonal to the direction of the longitudinal axis 20a. Further, in a case where the first three-way pipe 200 and the second three-way pipe 300 are projected onto a plane perpendicular to the direction of the longitudinal axis 20a, the branch pipe portion 204 and the straight pipe portion 303 are arranged at positions overlapping with each other. That is, as shown in the cross-sectional view of FIG. 6, the branch pipe portion 204 and the straight pipe portion 303 are arranged so that a part of the straight pipe portion 303 overlaps with a region where the branch pipe portion 204 is disposed.

Accordingly, since the first three-way pipe 200 and the second three-way pipe 300 are arranged at such a position, the balloon pipe line 104 and the air/water supply pipe line 102 can be arranged adjacent to each other in the height direction of the distal-end-part body 50. Therefore, the diameter of the distal-end-part body 50 can be reduced, so that the size of the distal-end-part body 50 can be reduced.

Further, since the straight pipe portion 303 is disposed closer to the distal end side than the branch position 202a in the direction of the longitudinal axis 20*a* as shown in FIG. 9, the pipe line portion 203 and the straight pipe portion 303 can be made close to each other in the direction of the arrow C orthogonal to the direction of the longitudinal axis 20*a*. Accordingly, since the balloon pipe line 104 and the air/ water supply pipe line 102 can be arranged close to each other in the height direction of the distal-end-part body 50, the diameter of the distal-end-part body 50 can be further reduced.

Furthermore, since the connecting pipe portion 206 and the connecting pipe portion 306 are arranged adjacent to each other in the direction of the longitudinal axis 20*a,* the length of the distal-end-part body 50 in the direction of the longitudinal axis 20*a* can be reduced.

Moreover, since the third offset distance c shown in FIG. 8 is set to be longer than the first offset distance a shown in FIG. 7, interference between the straight pipe portion 205 forming a part of the balloon-water supply pipe line 112 and the branch pipe portion 304 forming a part of the water supply pipe line 110 can be prevented even in a case where the connecting pipe portion 206 and the connecting pipe portion 306 are arranged adjacent to each other in the direction of the longitudinal axis 20*a* as described above.

Further, in the embodiment, the main pipe portion 202 and the branch pipe portion 204 are arranged along the first imaginary plane A as shown in FIG. 7 and the main pipe portion 302 and the branch pipe portion 304 are arranged along the second imaginary plane B as shown in FIG. 8. Furthermore, as the configuration where these pipe portions are arranged in the distal-end-part body 50, it is preferable that these pipe portions are provided so that the direction of the branch pipe portion 204 branched from the main pipe portion 202 and the direction of the main pipe portion 302 reaching the straight pipe portion 305 from the straight pipe portion 303 through the connecting pipe portion 306 three-dimensionally cross each other. That is, it is preferable that the first three-way pipe 200 and the second three-way pipe 300 are arranged so that the first imaginary plane A and the second imaginary plane B cross each other, that is, the first imaginary plane A and the second imaginary plane B are not parallel to each other. Accordingly, a narrow space formed above the light guides 128, the ultrasound cable 130, and the signal cable 132 as shown in FIG. 6 can be effectively used to arrange the first three-way pipe 200 and the second three-way pipe 300, as compared to configuration where the first three-way pipe 200 and the second three-way pipe 300 are arranged so that, for example, the first imaginary plane A and the second imaginary plane B are parallel to each other. Therefore, the size of the distal-end-part body 50 can be reduced.

Further, it is preferable that the main pipe portion 202, the branch pipe portion 204, and the straight pipe portion 303 are arranged along the same straight line E and the branch pipe portion 304 and the straight pipe portion 305 are arranged at positions away from the straight line E in a case where the first three-way pipe 200 and the second three-way pipe 300 are projected onto a plane D (see FIG. 6) perpendicular to the direction of the longitudinal axis 20*a*. Accordingly, the size of the distal-end-part body 50 in the direction of the arrow C orthogonal to the direction of the longitudinal axis 20*a* can be reduced as compared to a case where, for example, the main pipe portion 202, the branch pipe portion 204, the straight pipe portion 303, the branch pipe portion 304, and the straight pipe portion 305 are arranged along the same straight line E. Therefore, the diameter of the distal-end-part body 50 can be reduced, so that the size of the distal-end-part body 50 can be reduced.

Figures 10A, 10B:
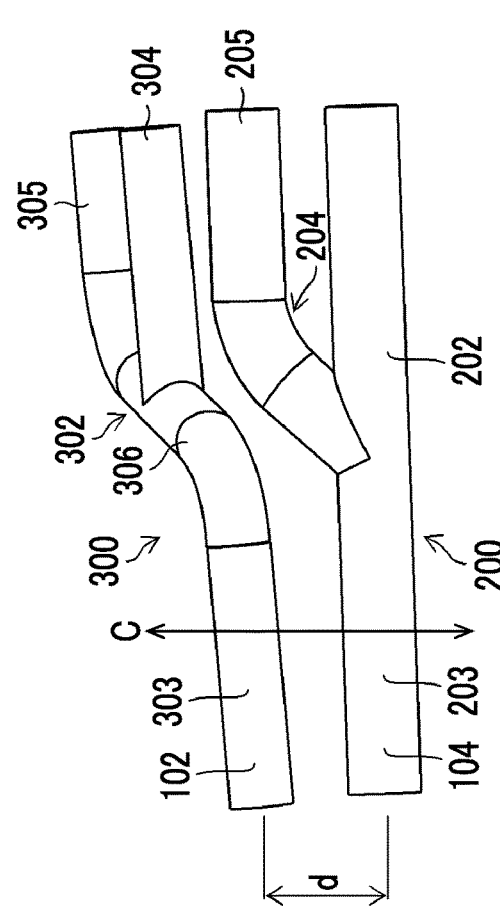
FIGS. 10A and 10B are diagrams illustrating the effects of the arrangement positions of the embodiment.

Here, effects obtained from the arrangement configuration of the embodiment will be described with reference to FIGS. 10A and 10B. FIG. 10A is a side view showing the arrangement configuration of the first three-way pipe 200 and the second three-way pipe 300 shown in FIG. 9, and FIG. 10B is a side view showing the arrangement configuration of two first three-way pipes 200 and 200 in a case where the first three-way pipe 200 is used instead of the second three-way pipe 300 as a comparative example.

In the arrangement configuration shown in FIG. 10B, an interval e between the main pipe portions 202 and 202 in the direction of the arrow C needs to be increased for the avoidance of interference between the two main pipe portions 202 and 202 in the direction of an arrow C orthogonal to the direction of the longitudinal axis 20*a* (see FIG. 9). Accordingly, the diameter of the distal-end-part body 50 is increased as much as an increase in the interval.

In contrast, in the arrangement configuration of the embodiment shown in FIG. 10A, the pipe line portion 203 and the straight pipe portion 303 are arranged adjacent to each other in the direction of the arrow C orthogonal to the direction of the longitudinal axis 20*a* (see FIG. 9) and the branch pipe portion 204 and the straight pipe portion 303 are arranged at positions overlapping with each other in a case where the first three-way pipe 200 and the second three-way pipe 300 are projected onto the plane D (see FIG. 6) perpendicular to the direction of the longitudinal axis 20*a*. Accordingly, the balloon pipe line 104 and the air/water supply pipe line 102 can be arranged adjacent to each other in the height direction of the distal-end-part body 50. Therefore, the diameter of the distal-end-part body 50 can be reduced, so that the size of the distal-end-part body 50 can be reduced. That is, as shown in FIG. 10A, an interval d between the pipe line portion 203 and the straight pipe portion 303 can be set to be shorter than the interval e between the main pipe portions 202 and 202 shown in FIG. 10B. Accordingly, the diameter of the distal-end-part body 50 can be reduced.

In other words, as shown in FIG. 9, the pipe line portion 307 closer to the air/water supply port 103 than the branch position 302*a* of the connecting pipe portion 306 is disposed closer to the distal end side than the connecting pipe portion 206 in the direction of the longitudinal axis 20*a,* and the branch pipe portion 204 and the straight pipe portion 303 are arranged at positions overlapping with each other in a case where the first three-way pipe 200 and the second three-way pipe 300 are projected onto the plane D (see FIG. 6) perpendicular to the direction of the longitudinal axis 20*a*. Accordingly, the diameter of the distal-end-part body 50 can be reduced. Further, since the pipe line portion 307 and the connecting pipe portion 206 are arranged adjacent to each other in the direction of the longitudinal axis 20*a,* the length of the distal-end-part body 50 in the direction of the longitudinal axis 20*a* can be reduced.

An aspect where the lower portion of the straight pipe portion 303 overlaps with the upper portion of the branch pipe portion 204 as shown in the cross-sectional view of FIG. 6 has been described as a preferred aspect in the embodiment, but an aspect where the straight pipe portion 303 is disposed is not limited thereto. For example, a position closer to the main pipe portion 202 than the arrangement position of the straight pipe portion 303 shown in FIG. 6 may be set as the arrangement position of the straight pipe portion 303.

Further, the straight pipe portion 305 is offset from the straight pipe portion 303 by the second offset distance b as shown in FIG. 8 in the embodiment, so that the straight pipe portion 305 can be disposed in a space shown in FIG. 6. Furthermore, configuration where one end of the straight pipe portion 305 and the other end of the straight pipe portion 303 are connected to each other using the first curved pipe portion 308 and the second curved pipe portion 310 is employed. Accordingly, even in a case where the straight pipe portion 305 is offset from the straight pipe portion 303, air supplied from the straight pipe portion 305 forming a part of the air supply pipe line 108 can be made to smoothly flow to the straight pipe portion 303 forming a part of the air/water supply pipe line 102.

Further, the connecting pipe portion 306 including the straight connecting pipe portion 312 has been illustrated in FIG. 8, but a connecting pipe portion 306 that directly connects one end of the second curved pipe portion 310 to the other end of the first curved pipe portion 308 without using the straight connecting pipe portion 312 can also be applied. In this case, the branch pipe portion 304 is connected to the first curved pipe portion 308 or the second curved pipe portion 310. Furthermore, in this case, the branch position 302a is a position which is provided on a pipe line portion including the first curved pipe portion 308 and the second curved pipe portion 310 and at which one end of the branch pipe portion 304 is connected.

Further, the main pipe portion 202 forms the balloon-drain pipe line 114 and the branch pipe portion 204 forms the balloon-water supply pipe line 112 as a preferred aspect in the embodiment, but the invention is not limited thereto. Since the balloon-drain pipe line 114 is a pipe line that is to be washed by the insertion of a brush after the use of the ultrasound endoscope 10, it is preferable that a main pipe portion 202 formed as a linear pipe line to allow the brush to be easily inserted is used as the balloon-drain pipe line 114. The balloon-drain pipe line 114 is a suction passage of the invention, and the balloon-water supply pipe line 112 is a water supply passage of the invention.

Furthermore, an example where the first pipe of the invention forms a pipe for a balloon and the second pipe of the invention forms an air/water supply pipe has been described in the embodiment, but the invention is not limited thereto. The first pipe and the second pipe may form other pipes.

The invention has been described above, but it is natural that the invention is not limited to the above-mentioned embodiment and may have various improvements and modifications without departing from the scope of the invention.

EXPLANATION OF REFERENCES

2: ultrasonography system
10: ultrasound endoscope
12: ultrasound processor device
14: endoscope processor device
16: light source device
18: monitor
20: insertion unit
20a: longitudinal axis
22: operation unit
24: universal cord
26: ultrasound connector
28: endoscope connector
30: light source connector
32: tube
34: tube
36: air/water supply button
36a: operation cap
38: suction button 38a: operation cap
42: angle knob
44: treatment tool insertion opening
50: distal-end-part body
52: bendable part
54: soft part
60: ultrasound observation unit
62: ultrasound transducer
64: balloon
68: locking groove
70: supply/discharge port
72: housing member
72a: side wall portion
72b: side wall portion
74: groove portion
80: endoscopic observation unit
82: observation portion
84: illumination portion
86: inclined surface portion
88: observation window
90: illumination window
92: nozzle
93: jet port
94: treatment tool outlet
96: standing base
100: treatment tool channel
102: air/water supply pipe line
103: air/water supply port
104: balloon pipe line
106: suction pipe line
108: air supply pipe line
110: water supply pipe line
112: balloon-water supply pipe line
114: balloon-drain pipe line
116: air supply source-pipe line
118: water supply tank
120: water supply source-pipe line
122: branch pipe line
124: suction pump
126: suction source-pipe line
128: light guide
129: air supply pump
132: signal cable
134: wire
200: first three-way pipe
200a: first pipe axis
202: main pipe portion
202a: branch position
203: pipe line portion
204: branch pipe portion
206: connecting pipe portion
300: second three-way pipe
300a: second pipe axis
302: main pipe portion
302a: branch position
304: branch pipe portion
306: connecting pipe portion
307: pipe line portion
308: first curved pipe portion
310: second curved pipe portion
312: straight connecting pipe portion

What is claimed is:

1. An ultrasound endoscope comprising:
an insertion unit having a tip portion;
an observation window disposed in the insertion unit, an image pickup element disposed corresponding to the observation window;

a first three-way pipe and a second three-way pipe disposed in the insertion unit;

a treatment tool channel disposed within the insertion unit;

a signal cable disposed in the insertion unit and connected to the image pickup element, wherein a first opening portion of the first three-way pipe and a second opening portion of the second three-way pipe are disposed on the tip portion, and the insertion unit has a first position on a proximal end thereof from the first opening portion, wherein in a circular cross-section at the first position of the insertion unit, the treatment tool channel, the first three-way pipe, and the second three-way pipe are closer to an outer peripheral surface of the insertion unit than to the signal cable, wherein in a circular cross-section, the first three-way pipe and the second three-way pipe are adjacent to each other, wherein the first three-way pipe is branched into a plurality of first pipe portions, and the second three-way pipe is branched into a plurality of second pipe portions, and wherein a first virtual surface where the plurality of first pipe portions is arranged and a second virtual surface where the plurality of second pipe portions is are arranged non-parallelly to each other.

2. The ultrasound endoscope according to claim 1, wherein in the circular cross-section, a first side is where the treatment tool channel is disposed with respect to the signal cable, and a second side is a side opposite to the first side, and wherein a portion of the plurality of first pipe portions and the plurality of second pipe portions are disposed on the second side with respect to the signal cable.

3. The ultrasound endoscope according to claim 2, wherein, in the circular cross-section, a third side is where the first three-way pipe is disposed with respect to the signal cable, and a fourth side is a side opposite to the third side, and wherein a portion of the second pipe portions is disposed on the fourth side with respect to the signal cable.

4. The ultrasound endoscope according to claim 2, wherein an ultrasound transducer is disposed at the tip portion, and an ultrasound cable is connected to the ultrasound transducer, and wherein in the circular cross-section, the ultrasonic cable is disposed on the first side of the signal cable.

5. The ultrasound endoscope according to claim 1, further comprising:

a first merging portion of the plurality of first pipe portions;

a second merging portion of the plurality of first pipe portions;

a treatment tool passing through the treatment tool channel;

a standing base and a wire disposed at an outlet of the treatment tool channel, wherein as the insertion unit is disposed in a linear manner, the insertion unit has a longitudinal axis, wherein the wire is configured to be pulled to move the treatment tool upward together with the standing base, wherein as the first merging portion and the second merging portion are projected on a vertical plane perpendicular to the longitudinal axis, projected positions of the first merging portion and the second merging portion are shifted in a vertical direction and in left and right directions in relative to the vertical plane.

6. The ultrasound endoscope according to claim 5, wherein the first three-way pipe is arranged in an order of the plurality of first pipe portions, the first merging portion, and a first straight pipe portion sequentially from the proximal end, wherein the second three-way pipe is arranged in an order of the plurality of second pipe portions, the second merging portion, a curved pipe portion, and second straight pipe portions sequentially from the proximal end, and wherein the second merging portion is located closer to the proximal end than the first merging portion.

7. The ultrasound endoscope according to claim 6, wherein as the second straight pipe portions and the plurality of first pipe portions are projected onto the vertical plane, the second straight pipe portions and one of the plurality of first pipe portions are overlapped by the curved pipe portion.

8. The ultrasound endoscope according to claim 1, further comprising:

a first merging portion of the plurality of first pipe portions and a second merging portion of the plurality of second pipe portions, wherein the first three-way pipe is arranged in an order of the plurality of first pipe portions, the first merging portion, and a first straight pipe portion sequentially from the proximal end, and the second three-way pipe is arranged in an order of the plurality of second pipe portions, the second merging portion, a curved pipe portion, and second straight pipe portions sequentially from the proximal end, wherein as the insertion unit is disposed in a linear manner, the insertion unit has a longitudinal axis, and wherein as the second straight pipe portions and the plurality of first pipe portions are projected onto a vertical plane perpendicular to the longitudinal axis, the second straight pipe portions and one of the plurality of first pipe portions are overlapped by the curved pipe portion.

9. The ultrasound endoscope according to claim 8, wherein the second merging portion is located closer to the proximal end than the first merging portion.

10. The ultrasound endoscope according to claim 1, further comprising:

a balloon mounting portion disposed at the tip portion to which a balloon is attached, wherein a first three-way tube is configured for supplying or discharging an ultrasound transmission medium to the balloon, and a second three-way tube is configured for supplying liquid and air to the observation window.

11. The ultrasound endoscope according to claim 10, wherein the balloon mounting portion is a locking groove.

12. The ultrasound endoscope according to claim 1, wherein the second three-way pipe is configured for supplying liquid and air to the observation window, wherein in the circular cross-section, a first side is where the treatment tool channel is disposed with respect to the signal cable, and a second side is a side opposite to the first side, wherein the plurality of second pipe portions is provided on the second side with respect to the signal cable, and wherein the second opening portion is on the first side with respect to the observation window.

13. The ultrasound endoscope according to claim 12, wherein in the circular cross-section, a third side is where the first three-way pipe is disposed with respect to the signal cable, and the second opening portion is disposed on the third side with respect to the observation window.

\* \* \* \* \*